US008554330B2

(12) United States Patent
Bradley et al.

(10) Patent No.: US 8,554,330 B2
(45) Date of Patent: Oct. 8, 2013

(54) COCHLEAR IMPLANTS (75) Inventors: Andrew Peter Bradley, Queensland (AU); Matthew Alexander Petoe, Queensland (AU); Wayne James Wilson, Queensland (AU)

(73) Assignee: The University of Queensland, Queensland (AU)

( * ) Notice: Subject to any disclaimer, the term of this patent is extended or adjusted under 35 U.S.C. 154(b) by 122 days.

(21) Appl. No.: 13/061,890

(22) PCT Filed: Sep. 2, 2009

(86) PCT No.: PCT/AU2009/001142
§ 371 (c)(1),
(2), (4) Date: May 18, 2011

(87) PCT Pub. No.: WO2010/025504
PCT Pub. Date: Mar. 11, 2010

(65) Prior Publication Data
US 2011/0238176 A1 Sep. 29, 2011

(30) Foreign Application Priority Data
Sep. 2, 2008 (AU) ................................ 2008904549

(51) Int. Cl.
*A61N 1/00* (2006.01)

(52) U.S. Cl.
USPC .......................................... 607/57; 607/137

(58) Field of Classification Search
None
See application file for complete search history.

(56) References Cited

U.S. PATENT DOCUMENTS

| 5,578,084 | A | 11/1996 | Kuzma et al. |
| 7,251,530 | B1 | 7/2007 | Overstreet et al. |
| 2004/0133371 | A1* | 7/2004 | Ziarani .................. 702/70 |
| 2005/0055069 | A1* | 3/2005 | Franck ................... 607/62 |
| 2006/0100672 | A1 | 5/2006 | Litvak |
| 2006/0287690 | A1* | 12/2006 | Bouchataoui et al. ........ 607/57 |

FOREIGN PATENT DOCUMENTS

| WO | 97/43871 | 11/1997 |
| WO | WO 2008/006164 A1 | 1/2008 |

OTHER PUBLICATIONS

Baumann, Uwe, et al, *Hearing Research*, 213 (2006) 34-42 "The cochlear implant electrode-pitch function."
Greenwood, D., *J. Acoust. Soc. Am.*, vol. 33, No. 10, Oct. 1961; pp. 1344-1356, "Critical Bandwidth and the Frequency Coordinates of the Basilar Membrane."
Dau, T., et al, *J. Acoust. Soc. Am.*, vol. 107, No. 3, Mach 2000, pp. 1530-1540, "Auditory brainstem responses with optimized chirp signals compensation basilar-membrane dispersion."
Fobel, O., et al, *J. Acoust. Soc. Am.*, vol. 116, No. 4, Pt. 1, Oct. 2004, pp. 2213-2222; "Searching for the optimal stimulus eliciting auditory brainstem responses in humans."
Elberling, C., et al, *Scand Audiol*, 13:187-197, 1984, "Quality Estimation of Averaged Auditory Brainstem Responses."

(Continued)

*Primary Examiner* — Carl H Layno
*Assistant Examiner* — Ankit Tejani
(74) *Attorney, Agent, or Firm* — Nixon & Vanderhye P.C.

(57) ABSTRACT

The invention relates to a method of generating a place-frequency map for accurate positioning of a cochlear implant whereby the place-frequency map is used to relate a physical position of the cochlear implant to a tonotopic map of the basilar membrane/spiral ganglion. The invention also relates to a method of electrically positioning of an already inserted cochlear implant within the cochlea to provide stimuli to only the parts of the cochlea that have reduced or no residual hearing.

30 Claims, 4 Drawing Sheets

(56) References Cited

OTHER PUBLICATIONS

International Search Report for PCT/AU2009/001142, mailed Dec. 4, 2009.

Dorman et al., An Electric Frequency-to-Place Map for a Cochlear Implant Patient with Hearing in Nonimplanted Ear, JARO, 2007, vol. 8, pp. 234-240.

* cited by examiner

COCHLEAR IMPLANTS

This application is the U.S. national phase of International Application No. PCT/AU2009/001142, filed 2 Sep. 2009, which designated the U.S. and claims priority to Australian Application No. 2008904549, filed 2 Sep. 2008, the entire contents of each of which are hereby incorporated by reference.

FIELD OF THE INVENTION

The present invention relates to the field of cochlear implants and in particular to a method of ensuring that the electrodes of a cochlear implant are correctly matched to the pitch perception of each particular patient. More particularly, the invention relates to a method for mapping the place-frequency (tonotopic) organization of the patient's basilar membrane (hair cells) and/or spiral ganglion so that the pitch of each electrode in the cochlear implant is matched to the patient's pitch perception.

BACKGROUND TO THE INVENTION

Loss of hearing has a serious impact on quality of life. Human ingenuity has been directed to addressing the problem of hearing loss, primarily by way of amplification devices. The confluence of modern micro-engineering and medical advances led to the development of aural implants that could directly convert sound waves to electrical impulses that could compensate for hearing loss.

On 1 Aug. 1978 Melbourne resident Rod Saunders became the first person in the world to receive a multi-channel cochlear implant. The cochlear implant is an electrical device that directly converts sound to electrical signals that directly stimulate the auditory system through an array of electrodes wound through the cochlea of a patient. Cochlear implants typically employ 24 electrodes although modern devices have been developed with up to 128 electrodes.

For people already functional in spoken language who lose their hearing, cochlear implants can be a great help in restoring functional comprehension of speech, especially if they have only lost their hearing for a short time. Cochlear implants (CI) have also been found to be useful in young children who have been born with significant hearing loss. In fact, cochlear implants have been provided to children as young as 4 months old.

Approximately half of the people who have received a cochlear implant are adults. Implantation into post-lingual adults, who developed speech before they lost their hearing, is particularly challenging as the electrodes on the implant must be aligned with the frequency specific areas of the patient's cochlea. In particular, it is important that the cochlear implant is inserted deeply enough into the cochlea so as to stimulate the lower frequency portions of the cochlea whilst avoiding damage to the cochlea wall itself. Damage to the cochlea wall may adversely affect residual hearing. Therefore, a perimodiolar insertion of implants is often preferred as they can be inserted more deeply into the scala timpani and closer to the modiolus.

A further problem relates to people with some residual low frequency hearing who are fitted with both a cochlear implant and an acoustic hearing aid, which is often referred to as bimodal amplification. A problem with bimodal amplification is that the sounds travel faster through the cochlear implant as electrical stimuli than the amplified sounds from the acoustic hearing aid. The result is that the sounds are received by the brain at fractionally different times which can lead to difficulties in word recognition. This is especially the case during binaural hearing, where the relative timing between the ears is important for source localisation, and is required for accurate sound perception, e.g., recognising speech in a noisy environment.

In addition, for patients with a partial hearing impairment, it is highly desirable to align the electrodes of the implant with the hair cells (or associated spiral ganglion) that have been damaged or lost. In this way, the electrodes stimulate the appropriate area on the cochlea, thus complementing the patient's remaining hair cells that are still functioning. Therefore, both accurate positioning and mapping of the implant's electrodes can assist effective rehabilitation of hearing loss. Furthermore, many patients who have low frequency residual hearing and are fitted with both a Cochlear implant and an acoustic hearing aid only require a certain range of frequencies to be amplified.

Currently cochlear implants are positioned by pushing the electrodes as far into the cochlea as considered necessary by the physician. In general, there is no attempt to accurately align the electrodes with particular parts of the cochlea. There have been modifications to the conventional linear cochlear electrode arrays to take a curved shape within the ear (see U.S. Pat. No. 5,578,084 assigned to Cochlear Ltd and University of Melbourne), but these variations still do not attempt any form of accurate positioning of the electrode array.

An electric frequency-place function—or better termed electrode-pitch function—is therefore of high importance for the design of the signal processing strategies implemented in cochlear implant speech processor devices. A close match of spectral information in the signal to the electrodes with the corresponding pitch perception of the patient contributes to a better acceptance of the sound of a cochlear implant and enhances the representation of spectral information (U. Baumann, A. Nobbe, The cochlear implant electrode-pitch function, Hearing Research 213 (2006) 34-42).

Currently most cochlear implants have 22 stimulating sites along their length. However, some newer implants host up to 126 stimulating sites, potentially giving greater tonal range and better frequency perception. In each case the remaining two electrodes are used as reference electrodes. Whilst implants with more electrodes could, in principle, deliver an improved perception of speech and other sounds in general, the previously described limitations of methods to position the implant mean that there is currently little perceived benefit to implants with a larger number of electrodes.

A study to relate the pitch of high-rate electrical stimulation delivered to individual cochlear implant electrodes to electrode insertion depth and insertion angle is reported in the Journal of the Association for Research in Otolaryngology (JARO, 2007, Vol 8 pp 234-240) to Dorman et al. This publication studied the results of a patient with a cochlear implant in one ear and some hearing in the other ear. The patient was asked to match tones applied to the implanted ear to tones applied to the non-implanted ear so that the implant could be programmed to match the pitch perception in each ear. This publication discloses that average data may be used to set up signal processors for implant patients however the disadvantage is that it would not be matched to a specific patient. Furthermore, the method attempts to match the pitch perception between the hearing ear and an implanted ear rather than matching a cochlear implant to the cochlea in which it is implanted.

US patent publication 2006/0100672 to Litvak, discloses a method of pitch matching cochlear implants inserted into both ears. However the method does not allow the cochlear implant to be optimised for an individual patient only to optimise the pitch perception of each cochlear implant, in each ear, to be similar.

International patent publication no WO9743871 discloses a method of mapping each electrode of a cochlear implant to a range of frequencies depending on where the cochlear is inserted into the cochlear. However this method is not based on residual hearing of an individual patient, rather it is based on image data obtained from a CT scan.

Therefore, there are three significant limitations that impede clinical use of cochlear implants for post-lingual adults with partial hearing loss:

1. The large inter-subject variation in cochlear physiology and cochlear implant insertion depth leads to uncertainty in the mapping/alignment of electrodes to the appropriate frequency/pitch specific cochlea/spiral ganglion nerve fibres for that individual patient;
2. The limited number of electrodes in most current implants limits the quality of speech and sound perceived by the patient; and
3. The lack of compensation for the timing differences between the arrival of acoustic and electrical stimuli when applied to patients with bimodal amplification.

OBJECTS OF THE INVENTION

It is an object of the present invention to overcome or at least ameliorate one or more of the above limitations including providing a method for accurately mapping pitch perception to the electrodes of a cochlear implant (CI).

It is a further object of the present invention to match the frequency of the stimulating sites of the electrode to the patient's pitch perception using information from their Auditory Brainstem Response (ABR).

The present invention may also be used to correct for timing differences between acoustic and electric stimuli in people with residual hearing who are suitable for combined electro-acoustic stimulation, i.e., the subject will have both a cochlear implant and an acoustic hearing aid (also known as bimodal amplification).

SUMMARY OF THE INVENTION

In one form, although it need not be the only or indeed the broadest form, the invention resides in a method of accurately correlating electrodes of a cochlear implant with a cochlea of a patient including the steps of:

Measuring a tonotropic response for residual hearing of the cochlea of the patient to obtain a place-frequency map describing a place-frequency structure of the cochlea; and Optimally aligning the electrodes of the cochlear implant with the place-frequency structure of the cochlea.

In a further form the invention resides in a method of generating a place-frequency map for accurate positioning of a cochlear implant whereby the place-frequency map is used to relate a physical position of the cochlear implant to a tonotopic map of the cochlea including the steps of:

1. Measuring a tonotopic response for the residual hearing of the cochlea of a patient to obtain a place-frequency map;
2. Inserting the cochlear implant according to the place-frequency map; and
3. Confirming the position of the cochlear implant accords to the measured place-frequency map, by electrical stimulation of the cochlear implant and auditory stimulation of the cochlea.

Alternatively the place-frequency map may be used to electrically position (i.e., map the pitch perception of each electrode) of an already inserted cochlear implant within the cochlea to provide stimuli to only the parts of the cochlea that have reduced or no residual hearing, including the following steps:

1. Measuring a tonotopic response for the residual hearing of the cochlea of a patient to obtain the place-frequency map; and
2. Mapping the electrodes of the cochlear implant according to the measured place-frequency map and by measuring an electro-acoustic response of the cochlea and implant.

Additionally, a delay may be measured between an electrical response and an acoustic response and the delay may be applied to the cochlear implant to improve binaural hearing.

More particularly, the invention relates to a method for mapping the place-frequency organization (tonotopic map) of the patient's basilar membrane and/or spiral ganglion so that the tonotopic map of the cochlear implant electrodes are specific to each individual patient. In this way, the cochlear implant may then be inserted or mapped onto the patient's cochlea so that the electrodes on the cochlear implant are optimally aligned to the place-frequency structure of their cochlea.

Additionally, the tonotopic map of the implant may be modified using the patient's Auditory Brainstem Response (ABR) to provide electrical stimulation only to areas of the cochlea that have either a reduced or no response. The tonotopic map may be modified to suit an individual by finding an upper limit of residual hearing (ULRH) and adjusting the position of a Greenwood Function to pass through this ULRH. Furthermore, the slope of the Greenwood Function may be modified so that it corresponds to the rise time of a patient specific chirp (rising frequency) stimulus. In another form of the invention the Greenwood Function may also be modified to fit a polynomial or more complex curve.

Further features and advantages of the present invention will become apparent from the following detailed description.

BRIEF DESCRIPTION OF THE DRAWINGS

To assist in understanding the current invention and to enable a person skilled in the art to put the invention into practical effect, preferred embodiments of the invention will be described by way of example only, with reference to the accompanying drawings, in which.

DETAILED DESCRIPTION OF THE INVENTION

Embodiments of the present invention reside primarily in method steps for acquiring a tonotopic map and using the map to either accurately position or map an electrode array of a cochlear implant. Furthermore, the present invention may be used to design a tailor made implant or create a range of cochlear implants which may then be selected for individual patients. Accordingly, the method steps have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

Figure 1:
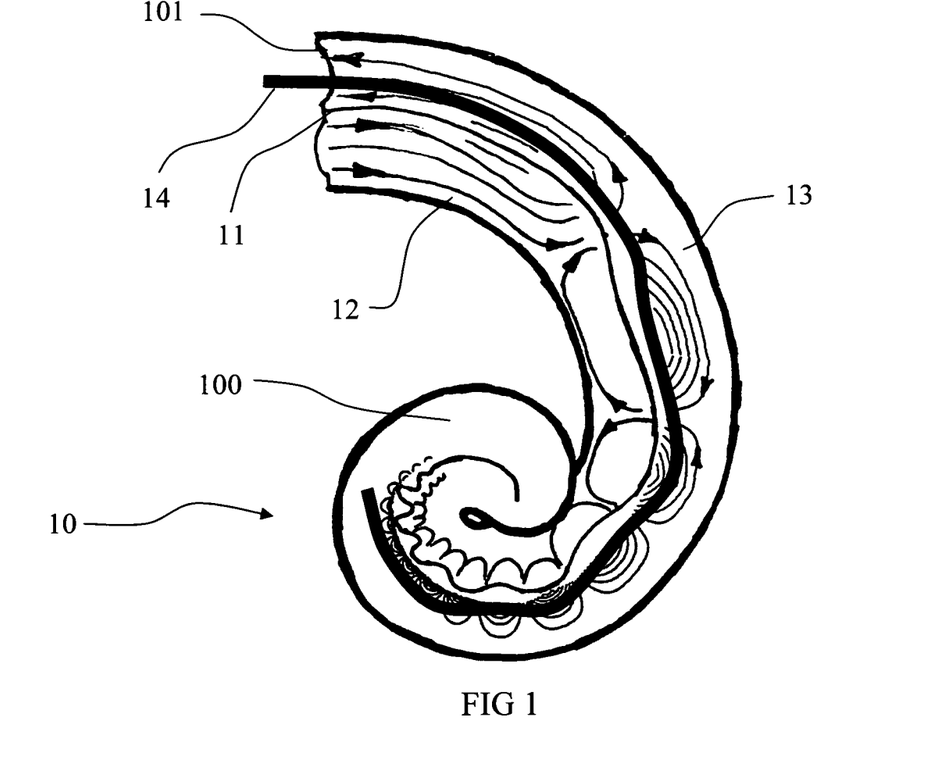
FIG. 1 is a sketch of an electrode array of a cochlear implant positioned in a cochlea.
Figure 2:
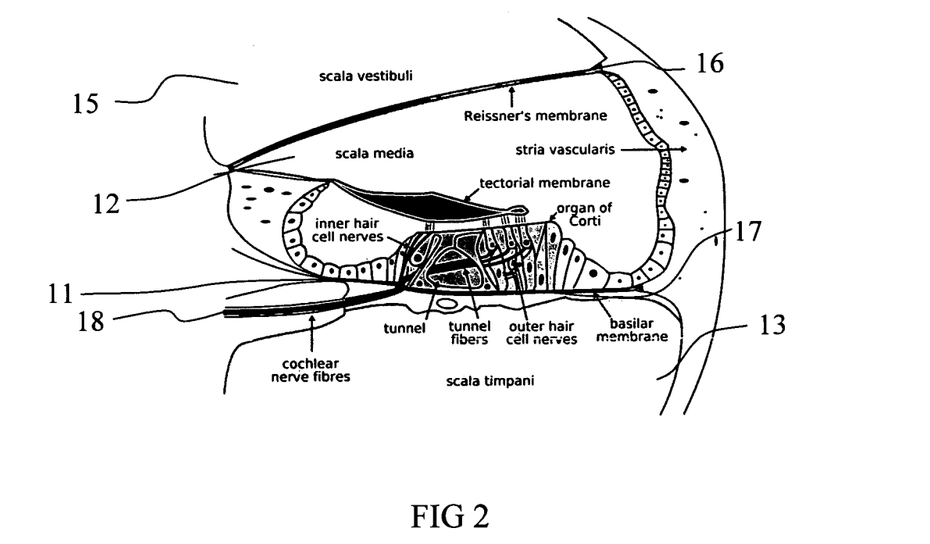
FIG. 2 is a sketch of a cross-section of an electrode array of a cochlear implant positioned in a cochlea.

The method of accurately positioning the cochlear implant (CI) will now be described with reference to FIGS. 1 and 2. FIG. 1 shows a schematic of a cochlea 10 showing the basilar membrane 11 separating the scala media 12 and the scala timpani 13. Conventionally, the electrode array 14 is positioned in the scala timpani 13 so as to contact the basilar membrane 11. More detail is shown in FIG. 2 which also shows the scala vestibuli 15 separated from the scala media 12 by Reissner's membrane 16. Hair cell nerves 17 are shown near the basilar membrane 11 and connecting to form the cochlea nerve 18.

The electrode array 14 may be of any known form although the inventors speculate that the electrode array design described in U.S. Pat. No. 5,578,084 would be suitable. The electrode array described in U.S. Pat. No. 5,578,084 comprises a first layer of flexible material that contains the electrodes and a second layer of polymer material that has a controlled rate of expansion when exposed to water. This electrode has the benefit that it can be correctly positioned in the manner described below then slowly expanded to fill the scala timpani 13, thus keeping it in the chosen position. Suitable electrodes will be known to persons skilled in the art.

It is known that the cochlea 10 performs the function of frequency dispersion by causing sound input at certain frequencies to vibrate at some locations and other frequencies to vibrate at other locations on the basilar membrane. It has been shown that high frequencies lead to maximum vibrations at the basal end 101 of the cochlea coil and low frequencies lead to maximum vibration at the apical end 100.

The "place-frequency map" has been described empirically by the Greenwood function (Greenwood, D D. "Critical Bandwidth and the Frequency Coordinates of the Basilar Membrane," Journal of the Acoustical Society of America, vol. 33, pp. 1344-1356, 1961). The inventors have found that accurate tonotopic (place-frequency) maps can be constructed using an evoked potential, such as the auditory brainstem response (ABR) technique described in their co-pending international application number PCT/AU2007/000969, titled Method of Acquiring a Physiological Response. The method is briefly described as: "A method for acquiring a physiological response from a test subject, particularly an auditory brainstem response, by presenting a plurality of stimuli, such as a Maximum Length Sequence, detecting electrophysiological signals in response to the stimuli, generating a recover signal based on the stimuli and determining the physiological response from the electrophysiological signals and the recovery signal".

In the first embodiment of the current invention the auditory brainstem response (ABR) provides a mechanism for indirectly measuring the tonotopic map for an individual. The latency of the ABR at specific stimulus frequencies can be used to derive a time/latency-frequency relationship, which can then be used to infer the required place-frequency map. One method of doing this is described in T. Dau, O. Wegner, V. Mellert, and B. Kollmeier, "Auditory brainstem responses with optimized chirp signals compensating basilar-membrane dispersion," J. Acoust. Soc. Am. 107 (3), March 2000. Once the place-frequency map is obtained it can be used to determine the correct position for an electrode array of a cochlear implant. The following procedure is followed:

1. A tonotopic (place-frequency) map of electrode insertion depth against cochlea nerve frequency is constructed for each patient using an evoked potential, such as the Auditory Brainstem Response (ABR);
2. A series of patient specific stimuli are generated that maximise the amplitude of the evoked potential, such as the Auditory Brainstem Response (ABR);
3. The cochlear implant electrode is inserted according to the patient specific tonotopic map of step 1; and
4. The correct positioning of the electrode is confirmed via a combination of electrical stimulation of the implant and auditory stimulation of the cochlea. The combined electro-acoustic stimulus is designed from the previously derived patient specific stimuli of step 2 and correct positioning is confirmed via the measurement of the evoked response, such as the Auditory Brainstem Response (ABR).

The inventors have found that the invention is most useful with 128 electrode arrays that provide 126 individual interfaces to the cochlea nerve fibres 18 over a length of approximately 20 mm. The electrode array is typically only placed sufficiently far into the cochlea for the electrical stimulation to be applied in areas of damage but without damaging any functional areas of the cochlea. Alternatively, short implants, around 10 mm in length, can be utilized.

In addition to positioning the cochlear implant accurately into the cochlea, the electrode array may be programmed to provide electrical stimuli only to regions of the cochlea that are unresponsive.

As mentioned above, Greenwood has proposed an empirical formula for the place-frequency response of the cochlea with distance from the apical end. The formula is:

$$f = \int_0^x \Delta f_{cb} = A(10^{ax} - K)$$

Where:
 f is the characteristic frequency of the sound in hertz;
 A is a scaling constant between the characteristic frequency and the upper frequency limit of hearing for the species;

a is the slope of the straight-line portion of the frequency-position curve, which has shown to be conserved throughout all investigated species after scaling for the length of the cochlea. Typically, a=0.06;

x is the length in millimetres from the apical end of the cochlea to the region of interest normalized by the total length in millimetres of the cochlea spiral;

K is a constant of integration that represents the divergence from the log nature of the curve and is determined by the lower frequency audible limit in the species. The Greenwood Function (GF) is often simplified by assuming that K has a value of zero.

Whilst it is generally accepted that the Greenwood function accurately predicts the place-frequency relationship for normal acoustic hearing of the hair cells along the basilar membrane there are a number of complications when this formula is applied to the placement and mapping of cochlear implants:

The place-frequency map is known to change with stimulus intensity; and

The Greenwood Function requires modification to describe the place-frequency map of the spiral ganglion, which are the target nerve cells in the perimodiolar insertion of cochlear implants.

Therefore, in the second embodiment of the current invention it is envisaged that the Greenwood function can be adapted to construct a formula that is more closely matched with the auditory brainstem response of an individual patient and so create the best performing implant. In particular, the Greenwood function may be "shifted" (via an offset to the variable x), so that it exactly passes through (that is, complies with) a measured place-frequency point. Clearly, this is equivalent to physically changing the insertion depth of the implant, but requires only a change to the electrode-pitch map. However, if more than one place-frequency point can be measured, then the slope of the Greenwood function can also be modified (by altering the variable a) so that the place-frequency map is both shifted and either "stretched" or "compressed." With more points, the Greenwood function may be modified to fit a polynomial or more complex curve. In this way, the adapted Greenwood function can then be used to program the cochlear implant to provide stimuli only to the parts of the cochlea that have either a reduced or no function and according to the pitch perception of the patient. In the current invention this is done by following steps:

1. Designing a customized (rising frequency) chirp that maximizes the ABR amplitude from the residual hearing; and
2. Applying an electrical stimulus to an individual electrode of the CI followed approximately 5 ms later by the application of the acoustic (customized chirp) stimulus designed in step 1; and
3. Measuring the acoustic delay. This step details a method of improving binaural response because the electrical signals provided to the cochlear implant travel faster than the auditory signals.

Steps 1 and 2 above may be used to program which electrodes of the cochlear implant are stimulated depending upon the amount of residual hearing along different areas of the cochlea. Step 3 details a method of improving the patient's binaural response because the electrical signals provided to the cochlear implant travel faster that the auditory signals.

Each of the above steps will now be described in detail.

Step 1: Measure Place-Frequency Map of Residual Hearing

Designing a custom chirp that maximizes ABR amplitude from the residual hearing can either be done pre-operatively or post-operatively with a non-stimulated cochlear implant. In the preferred embodiment the custom chirp is designed by:

a. Applying a rising frequency acoustic chirp stimulus to elicit an ABR;
b. Reducing the upper frequency of the chirp until a reduction in ABR amplitude is observed. In this way, the bandwidth of the chirp is reduced and the upper frequency of residual hearing (UFRH) can be obtained. The bandwidth of the chirp may be reduced by applying a temporal window function, for example a Hanning window or Hamming window or any other suitable window, to the high frequency portion of the chirp. Additionally, the bandwidth of the chirp may be estimated from the patient's audiogram that relates hearing level (dBHL) to pure-tone frequency;
c. Adjusting the frequency rise-time of the chirp that further maximises the ABR amplitude as follows:

The travelling time on the basilar membrane (BMtime in seconds) is given by:

$$BMtime = a\left(\left(\frac{f}{1000}\right)^{-b}\right)$$

where:
f is the frequency in Hz; and
a and b are constants to the equation.

The constant 'b' is initially fixed at 0.413, according to the literature of Fobel, O and Dau, T [Searching for the optimal stimulus eliciting auditory brainstem responses in humans, (2004) 116 *Journal of the Acoustical Society of America*, pp 2213-2222].

The constant 'a' is now considered a variable and optimised for a particular patient. One way is by trialling a series of three chirps with three different values of 'a' and recording their ABR. Clearly, an exhaustive search evaluating all possible values of 'a' would be time inefficient. Instead a simple search strategy is employed that evaluates three values of 'a' (different chirps). This search is then modified until an optimal value of 'a' is found. To those skilled in the art it is obvious that there are numerous search strategies suitable for this purpose.

Initially the first three chirps are selected such that the median-length chirp is as per Fobel et al and the maximum and minimum length chirps are up to 1 millisecond greater or less than the median-length chirp respectively.

The 'window-size' of the search is the time-difference between the temporal length of the maximum and minimum length chirps, and the 'window-centre' of the search is the temporal length of the median-length chirp.

The amplitude/quality of the recorded ABR elicited by each of the three chirps is analysed in real time and when a clear distinction is evident in the performances of the three chirps, the scope of the search is adjusted accordingly. An algorithm is used to adjust the scope as follows:

i) If the median-length chirp has the highest quality, then the window-size is halved. That is, maximum and minimum length chirps are both moved closer to the median length chirp. Otherwise;
ii) The window-centre is adjusted to match the temporal length of the 'highest-quality' chirp. That is, the median length chirp is adjusted to be equal to either the minimum or maximum length chirp depending on which one resulted in the highest quality. The search window is then centred on this new median length chirp.

In the case of ii) above, the window-size remains fixed at the most recent value.

This algorithm progresses until the limits of the 'quality-test' accuracy are reached. That is, there is no longer a significant difference between the measured quality/amplitude for the different chirp lengths. In the current embodiment the 'Quality' is determined using an Fsp-test for each ABR recording. An Fsp-test is a measure of the signal to noise ratio of the ABR and hence is an estimate of ABR quality. The slope of the Fsp is analysed to determine which stimuli are recruiting the maximal number of synchronous neuron-firings at each elicitation.

Figure 5:
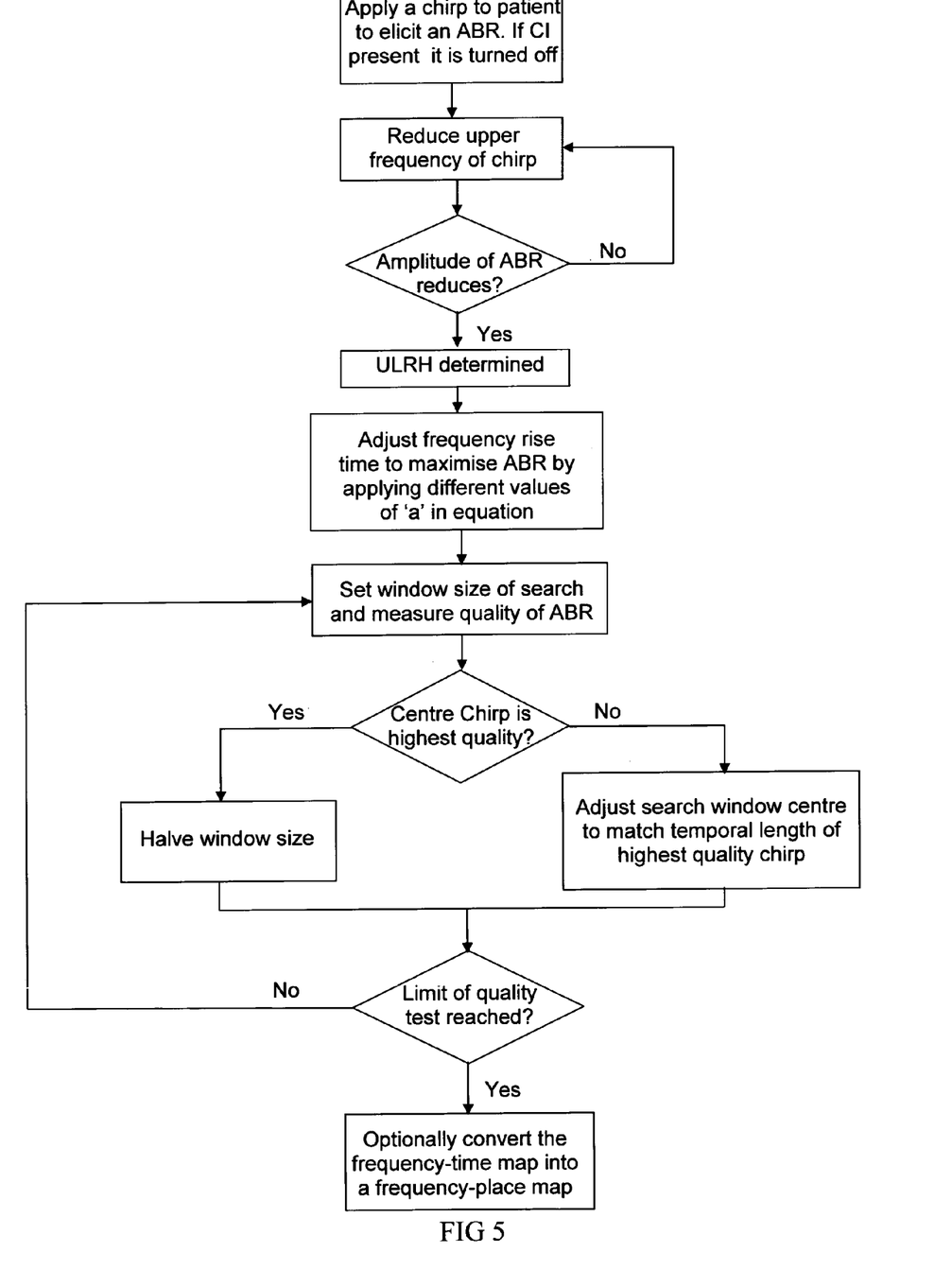
FIG. 5 is a flow chart of a process for generating a custom chirp stimulus for application in measuring a patient specific tonotopic map for cochlear implants.

FIG. 5 shows a flow chart showing the process of designing and applying a custom chirp to a cochlear implant as described in step 1 according to a first method of establishing an optimum value of 'a'.

In a second method, the constant 'a' may be optimised for a particular patient by trialling a series of chirps and analysing the relationship between chirp duration and response latency. In this case, an optimised chirp is one which adequately compensates for the travel time of each frequency component of the chirp in such a manner that the response from the highest frequency component occurs synchronously with the response from the lowest frequency component. An example of a poorly optimised chirp is one which elicits a response before the stimulus has ended. A premature response would indicate that the travel time on the basilar membrane is shorter than the duration of the stimulus. Therefore, the optimisation of the constant 'a' is based on the relationship between expected travel time on the basilar membrane and duration of the chirp stimulus.

Initially the response to a 'click', a tone-burst, or a falling-frequency chirp is used to elicit a response. An estimate of expected basilar membrane travel time is then obtained from the latency of peaks in this evoked response, allowing for any adjustments that may be required to compensate for headphone characteristics, the hearing characteristics of the test subject, or for acquisition parameters such as stimulus intensity.

The first rising-frequency candidate chirp to be tested would be selected such that the chirp length is as per Fobel et al. A comparison would be made between the previously determined 'expected travel time' and the response elicited by the candidate chirp. The constant 'a' would then be iteratively adjusted until an optimal relationship was established between the latency of the candidate chirp response, the length of the candidate chirp, and the expected basilar membrane travel time.

An algorithm is used to adjust the chirp length as follows:
i) If the length of the chirp is greater than the difference between the latency of its response and the expected travel time then the length of the chirp is reduced. Otherwise;
ii) If the length of the chirp is less than the difference between the latency of its response and the expected travel time then the length of the chirp is increased.

This algorithm progresses until the limits of measurement accuracy are reached (for example, ±0.2 ms). That is, the difference between the latency of the chirp response and the expected travel time is minimized. The limits of the algorithm may also be reached when the length of the chirp reaches a lower limit, such that the chirp becomes too similar in nature to a click. In this event it may be necessary to recalculate the expected travel time and begin the algorithm again.

Figure 6:
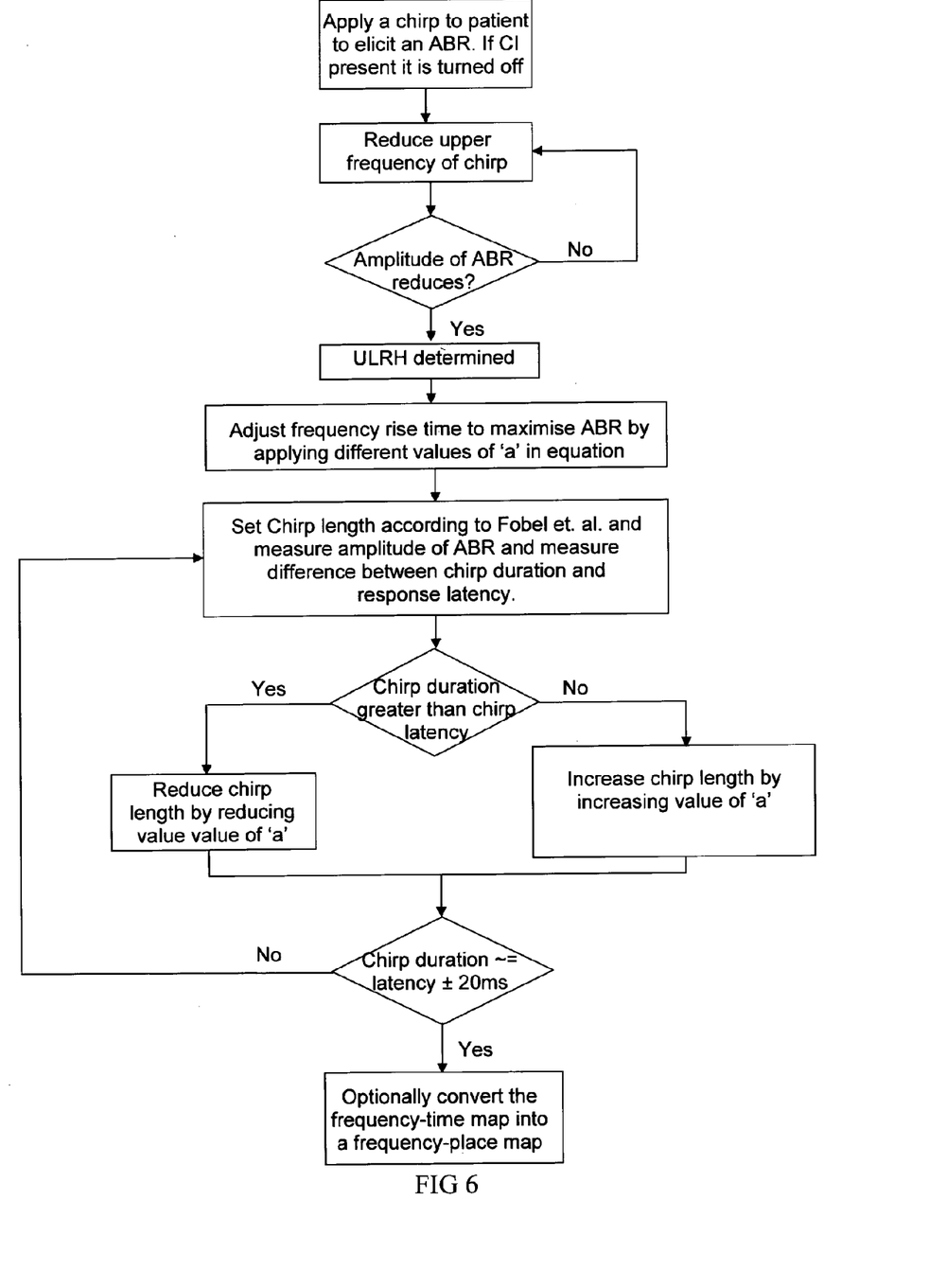
FIG. 6 is a flow chart of a further process for generating a custom chirp stimulus for application in measuring a patient specific tonotopic map for cochlear implants.

FIG. 6 shows a flow chart showing the process of designing and applying a custom chirp to a cochlear implant as described in step 1 according to a second method of establishing an optimum value of 'a'.

Step 2: Adjust Place-Frequency Map of Cochlear Implant

An electrical stimulus is applied to an individual electrode of the cochlear implant (CI) followed approximately 5 ms later by the application of the acoustic (custom chirp) stimulus designed in step 1. This will evoke a combined electrical ABR (EABR) and acoustic ABR (AABR). The AABR occurs approximately 6-7 ms later than the EABR. This electro-acoustic stimulus may be repeated at a rate of approximately 20 Hz, or every 50 ms, and individual responses may be averaged. Using this method, when an electrode is stimulated that coincides with an area of the cochlea that has residual (acoustic) hearing, the AABR amplitude will be significantly diminished. That is, the electrical stimulus will excite neurons related to remaining hair cells on the cochlea and, as the acoustic stimulation occurs within the refractory period of the neurons, there will be a significant reduction in the number of neurons able to respond to the acoustic stimulus, resulting in a significant reduction in AABR amplitude.

The electrical stimulus is then applied to each electrode starting from the base to the apex of the cochlear implant until the AABR amplitude is diminished. Electrodes that produce a reduction in AABR amplitude relate to electrodes that should not be mapped to specific frequency channels in the implant. In this way, the most apical electrode that does not result in a reduction in AABR amplitude can be assigned a frequency just above the upper frequency of residual hearing (UFRH), as measured in step 1. The most basal electrode that does cause a reduction in AABR amplitude may then be used to relate the position of this electrode (the upper place of residual hearing, UPRH) to a specific frequency, the UFRH. Note that the distance, in mm, of each electrode from the base of the implant is known. In this way, the remaining electrodes (towards the base of the implant/oval window of the patient) can be assigned corresponding frequencies utilising a modified Greenwood function, as illustrated below.

Figure 3:
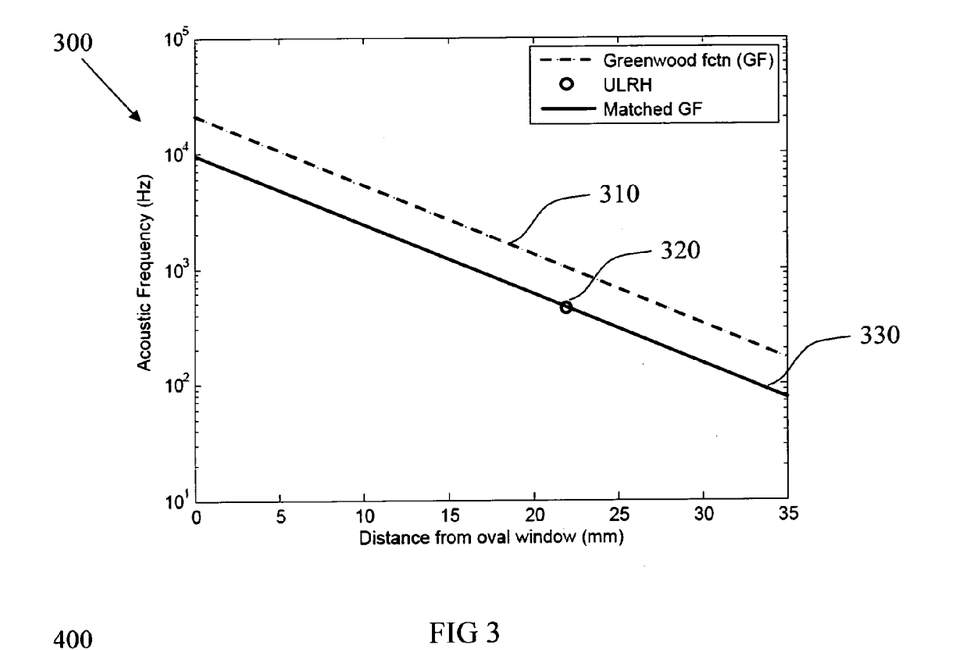
FIG. 3 is a tonotopic map showing the variation of acoustic frequency with distance from the round window along the Basilar Membrane of a cochlea. In particular, it shows a generic tonotopic map as specified by the Greenwood function and a modified (patient specific) Greenwood function matched to the patient's upper limit of residual hearing (ULRH)

A tonotopic map 300 is shown in FIG. 3 showing the variation of acoustic frequency with distance from the oval window, being the entrance to the apical end of the cochlea along the basilar membrane (BM). A dotted line 310 shows a simplified Greenwood function (where K=0) for the range of measurement frequencies. Point ULRH 320 is the Upper Limit of Residual Hearing (ULRH) found from the Upper Frequency of Residual Hearing (UFRH) in step 1 and the Upper Place of Residual Hearing (UPRH) in step 2. The solid line 330 shows the modified Greenwood function that corresponds to the measured ULRH. In the current embodiment the Greenwood Function is modified by calculating the difference, delta, in mm between the distance of an electrode assigned to the ULRH (UPRH) and the distance predicted by the Greenwood Function (x_green).

$$f = A^*(10\char`\^(a^*(x+\text{Delta})) - K)$$

By re-arranging the Greenwood Function (assuming K=0), a distance from the apical end of the cochlea (x_green) for a characteristic frequency, f_match, can be calculated as follows:

$$x\_green = (\log 10(f\_match) - \log 10(A))/a$$

For example, the theoretical upper frequency of hearing is 20,823 Hz, which occurs 35 mm from the apical end of the cochlea, that is at x_green=35 mm. Therefore, a person with un-impaired hearing will have a Delta of approximately zero. For patients with impaired hearing, the upper limit of hearing is further from the oval window and hence Delta is lengthened, and is given by:

Delta=$x$_green−(35−UPRH).

Figure 4:
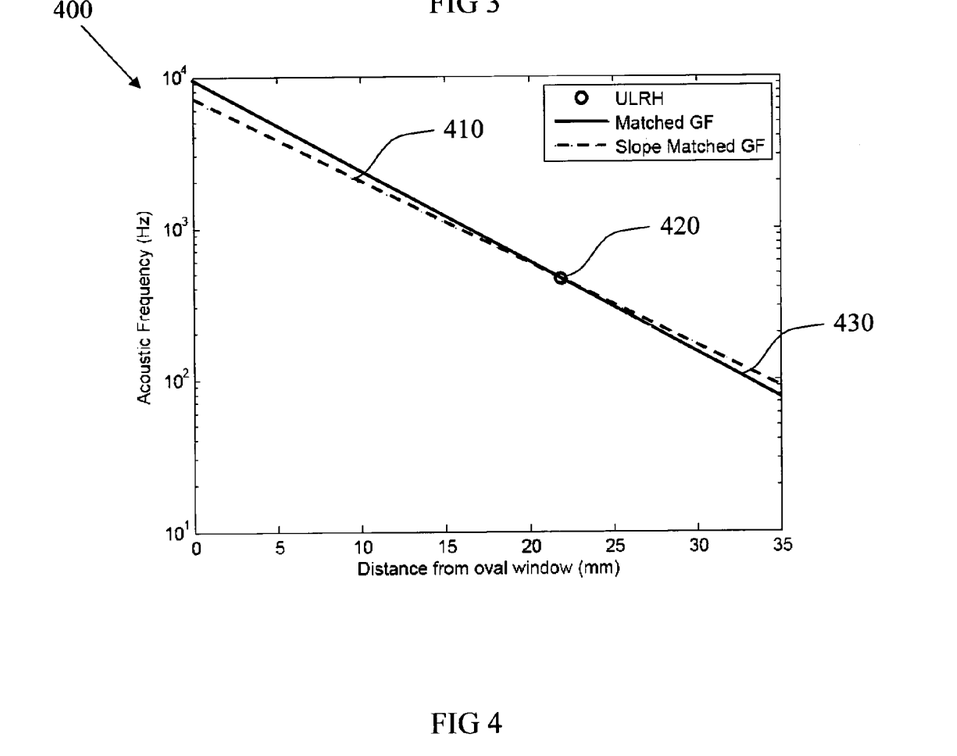
FIG. 4 is a modified tonotopic map of FIG. 3, where the Greenwood function is further modified so that its slope also matches the measured patient's tonotopic map.

FIG. 4 shows a tonotopic map 400 where, in addition to matching the Greenwood function 430 to the ULRH 420, the slope is also modified, to form a "slope matched" Greenwood Function 410, so that it corresponds to the rise time of the custom chirp designed in step 1c above.

The slope of the Greenwood function is determined by the parameter 'a' in the Greenwood Function and can be modified in a number of ways. In the current embodiment of the invention it is assumed that increases, or decreases, in chirp length away from the default 10 millisecond length chirp (equivalent, at the same dB Sound Level, to that described by Fobel, O., and Dau T, ["Searching for the optimal stimulus eliciting auditory brainstem responses in humans," J. Acoust. Soc. Am. 116 (4), Pages: 2213-2222, October 2004] relate to equivalent changes in basilar membrane length away from the normative 35 mm (as per the Greenwood function). In this way, a change in chirp rise time, delta_t (ms), results in a change in basilar membrane length of delta_x (mm) of 35*(delta_t/10). Therefore, to match the length of the basilar membrane to the rise time of the chirp the Greenwood function is firstly rearranged to estimate a new value for the slope parameter, new_a, that is:

new_$a$=(log 10($f$_upper)−log 10($A$))/(35+delta_$x$), where f_upper is the theoretical upper frequency limit of hearing, 35 mm from the apical end of the cochlea, as estimated by the Greenwood Function as f_upper=20,823 Hz.

When the slope of the Greenwood function is changed, it must still pass through the ULRH (that is, the UPRH at UFRH) on x_green, that is:

new_$x$_green=(log 10($f$_match)−log 10($A$))/new_$a$.

Next the difference between the measured ULRH and that estimated from the Greenwood function is recalculated as follows:

new_Delta=new_$x$_green−(35−UPRH).

This allows the position-frequency function matched on both the ULRH and custom chirp rise time (that is, the slope matched Greenwood function) to be calculated from the following:

$f=A*(10\hat{\ }(\text{new}\_a*(x+\text{new\_Delta}))-K)$.

The inventors realise that other methods in addition to the above described methodology may be used to estimate the slope matched Greenwood function. In particular, the above methodology assumes that the sounds propagate as a travelling wave along the basilar membrane at constant velocity, i.e., no energy dispersion. This is clearly a simplistic assumption and so one based on constant deceleration or a model of basilar membrane dispersion such as that in Dau, O. Wegner, V. Mellert, and B. Kollmeier, "Auditory brainstem responses with optimized chirp signals compensating basilar-membrane dispersion," J. Acoust. Soc. Am. 107 (3), March 2000, may be more appropriate.

Step 3: Measure Acoustic Delay

The acoustic delay may be measured by:
  a. Applying an (impulsive) electrical stimulus to the UPRH electrode determined in step 2 and the acoustic stimulus designed in step 1 at the same time. This will produce an Electrical ABR approximately 1 ms earlier than the Acoustic ABR; and
  b. Introducing an increasing delay before the presentation of the electrical stimulus, by approximately 1 ms, so that the Electrical ABR and Acoustic ABR occur at the same time (latency) and the resulting electro-acoustic ABR (E-AABR) has maximal amplitude/quality. The delay required to produce maximal E-AABR amplitude is the delay required to synchronise the presentation of the electrical stimulus in the cochlear implant to the acoustic stimuli in the part of the cochlea with residual hearing. Note and additional delay may also be required to compensate for any additional delay due to the acoustic hearing aid.

Measuring the acoustic delay detailed in step 3 above may also be useful for setting a correct time separation for improved binaural response and improved directionality perception by adjusting the time delay between each ear. The inventors have recognized that a timing problem arises due to the faster transit time of electrical signals compared to auditory signals. This would lead to confused signals being sent to the brain unless corrected. The inventors speculate that the brain may be able to correct the anomalies in patients that are post-linguistic but also propose suitable algorithmic delays be included in the signal processing algorithms of the cochlear implant to compensate for the identified timing issue using the value of the delay obtained from step 3.

In the above description, the amplitude of an ABR is commonly viewed as the amplitude of the primary wave (wave V) and for acoustic stimuli occurs with a latency of approximately 6 ms. In addition, an alternate measure of ABR amplitude/quality is ABR signal-to-noise ratio (SNR) which may be measured using the Fsp test (for details, see the publication "Quality estimation of Average Auditory Brainstem Responses", Scandinavian Audiology 13:187-197, 1984 by C. Elberling and M. Don).

It will be appreciated that the custom chirp designed in Step 1 may also be designed by measuring wave V latency to tone-burst stimuli for various frequencies or via the GHI-NOMA protocol (for details, see the publication "A System to Generate Patient-Specific Stimuli for use with the Auditory Brainstem Response Test," 29th IEEE Engineering in Medicine and Biology Society (EMBS) Annual International Conference, Lyon, France, August 2007 by M A. Petoe, A P. Bradley, W. Wilson which publication is incorporated herein by reference).

It will also be appreciated that another way to measure the electrode-pitch function is to gain data of pitch matching experiments from subjects with an implant in one ear and considerable residual acoustic hearing in the other (non-implanted) ear. For details, see the publication, "An Electric Frequency-to-place Map for a Cochlear Implant Patient with Hearing in the Non-implanted Ear", JARO 8: 234-240 (2007) by M. F. Dorman, T. Spahr, R Gifford, L. Loiselle, S. McKarns, T. Holden, M. Skinner, & C. Finley which publication is incorporated herein by reference.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:

1. A method of accurately correlating electrodes of a cochlear implant with a patient's cochlea within which the cochlear implant is to be implanted, the method including the steps of:
   measuring a tonotopic response for residual hearing of the cochlea of a patient to obtain a place-frequency map describing a place-frequency structure of the cochlea of a patient; and
   optimally aligning the electrodes of the cochlear implant with the place-frequency structure of the cochlea of a patient.

2. The method of claim 1 wherein optimally aligning the electrodes of the cochlear implant with the place-frequency structure of the cochlea of a patient includes measuring an electro-acoustic response of the cochlea of a patient and the cochlear implant and providing electric stimuli to only the parts of the cochlea of a patient that have reduced or no residual hearing.

3. The method of claim 2 wherein an electrode corresponding to an Upper Frequency of Residual Hearing is an Upper Place of Residual Hearing and electrodes from the Upper Place of Residual Hearing to an end of the cochlear implant are mapped according to a modified Greenwood Function.

4. The method of claim 3 including a step of modifying a slope of the modified Greenwood Function so that the modified Greenwood Function passes through the Upper Frequency of Residual Hearing.

5. The method of claim 3 including a step of modifying the modified Greenwood Function to fit a polynomial or more complex curve.

6. The method of claim 3 including a step of modifying the slope of the modified Greenwood Function to correspond with a rise time of a patient specific rising frequency chirp.

7. The method of claim 2 including steps of evoking an electro-acoustic response by:
   designing a custom rising frequency chirp corresponding to a maximum Auditory Brainstem Response of the patient; and
   applying an electrical stimulus to the electrode of the cochlear implant and later applying the custom rising frequency chirp.

8. A method of accurately correlating electrodes of a cochlear implant with a patient's cochlea within which the cochlear implant is to be implanted, the method including the steps of:
   measuring a tonotopic response for residual hearing of the cochlea of a patient to obtain a place-frequency map describing a place-frequency structure of the cochlea of a patient;
   optimally aligning the electrodes of the cochlear implant with the place-frequency structure of the cochlea of a patient, wherein optimally aligning the electrodes of the cochlear implant with the place-frequency structure of the cochlea of a patient includes measuring an electro-acoustic response of the cochlea of a patient and the cochlear implant and providing electric stimuli to only the parts of the cochlea of a patient that have reduced or no residual hearing;
   evoking an electro-acoustic response by:
      designing a custom rising frequency chirp corresponding to a maximum Auditory Brainstem Response of the patient; and
      applying an electrical stimulus to the electrode of the cochlear implant and later applying the custom rising frequency chirp;
   reducing an upper frequency of the custom rising frequency chirp until a reduction in Auditory Brainstem Response amplitude is observed to determine the Upper Frequency of Residual Hearing; and
   adjusting a frequency rise time of the custom rising frequency chirp to further maximise an Auditory Brainstem Response amplitude of the patient.

9. The method of claim 8 further including steps of:
   analysing the Auditory Brainstem Response where an acoustic evoked part of the Auditory Brainstem Response is evoked by the custom rising frequency chirp that causes the maximum Auditory Brainstem Response of the patient; and
   providing stimuli to the electrodes of the cochlear implant that do not produce a reduction in an electric evoked Auditory Brainstem Response.

10. The method of claim 9 including a step of adjusting the frequency rise time of the custom rising frequency chirp by:
    adjusting a window size of the custom rising frequency chirp to maximise the Auditory Brainstem Response amplitude.

11. The method of claim 9 including a step of adjusting the frequency rise time of the custom rising frequency chirp by:
    adjusting a length of the custom rising frequency chirp so that an expected travel time on a basilar membrane of the cochlea of a patient is about equal to a latency of a response of the custom rising frequency chirp to maximise the Auditory Brainstem Response amplitude.

12. The method of claim 1 wherein the cochlear implant is implanted in the cochlea of a patient according to the place-frequency map so as to achieve optimal alignment of the electrodes of the cochlear implant with the place-frequency structure of the cochlea of a patient.

13. The method of claim 12 further including a step of confirming a position of the cochlear implant according to the place-frequency map by electrical stimulation of the cochlear implant and auditory stimulation of the cochlea of a patient.

14. The method of claim 13 further including a step of measuring the Auditory Brainstem Response to the electrical stimulation of the cochlear implant and the auditory stimulation of the cochlea of a patient.

15. The method of claim 14 wherein the auditory stimulation is patient specific to maximize the Auditory Brainstem Response of the patient.

16. The method of claim 1 further including steps of:
    measuring a delay between an electrical response of the cochlear implant and an acoustic response of the cochlea of a patient; and
    applying the delay to the cochlear implant to improve binaural hearing.

17. The method of claim 7 wherein the custom rising frequency chirp is applied about 5 milliseconds after the electrical stimulus.

18. The method of claim 8 further including steps of:
    analysing the Auditory Brainstem Response where an acoustic evoked part of the Auditory Brainstem Response is evoked by the custom rising frequency chirp that causes a maximum Auditory Brainstem Response of the patient; and
    providing stimuli to the electrodes of the cochlear implant that do not produce a reduction in an electric evoked Auditory Brainstem Response.

19. The method of claim 18 further including a step of adjusting the frequency rise time of the custom rising frequency chirp by:
adjusting a window size of the custom rising frequency chirp to maximise the Auditory Brainstem Response amplitude.

20. The method of claim 18 further including a step of adjusting the frequency rise time of the custom rising frequency chirp by:
adjusting a length of the custom rising frequency chirp so that an expected travel time on a basilar membrane of the cochlea of a patient is about equal to a latency of a response of the custom rising frequency chirp to maximise the Auditory Brainstem Response amplitude.

21. The method of claim 8 wherein the cochlear implant is implanted in the cochlea of a patient according to the place-frequency map so as to achieve optimal alignment of the electrodes of the cochlear implant with the place-frequency structure of the cochlea of a patient.

22. The method of claim 21 further including a step of confirming a position of the cochlear implant according to the place-frequency map by electrical stimulation of the cochlear implant and auditory stimulation of the cochlea of a patient.

23. The method of claim 22 further including a step of measuring the Auditory Brainstem Response to the electrical stimulation of the cochlear implant and the auditory stimulation of the cochlea of a patient.

24. The method of claim 23 wherein the auditory stimulation is patient specific to maximize the Auditory Brainstem Response of the patient.

25. The method of claim 8 further including steps of:
measuring a delay between an electrical response of the cochlear implant and an acoustic response of the cochlea of a patient; and
applying the delay to the cochlear implant to improve binaural hearing.

26. The method of claim 8 wherein an electrode corresponding to an Upper Frequency of Residual Hearing is an Upper Place of Residual Hearing and electrodes from the Upper Place of Residual Hearing to an end of the cochlear implant are mapped according to a modified Greenwood function.

27. The method of claim 8 further including a step of modifying a slope of the modified Greenwood Function so that the modified Greenwood Function passes through the Upper Frequency of Residual Hearing.

28. The method of claim 8 further including a step of modifying the modified Greenwood Function to fit a polynomial or more complex curve.

29. The method of claim 8 further including a step of modifying the slope of the modified Greenwood Function to correspond with a rise time of a patient specific rising frequency chirp.

30. The method of claim 8 wherein the custom rising frequency chirp is applied about 5 milliseconds after the electrical stimulus.

* * * * *